United States Patent
Roh et al.

(10) Patent No.: US 6,310,239 B1
(45) Date of Patent: *Oct. 30, 2001

(54) PROCESS FOR MANUFACTURING TEREPHTHALIC ACID

(75) Inventors: Hang-Duk Roh, Kyungki-do; Dongmok Bae, Seoul, both of (KR)

(73) Assignee: Sunkyong Industries Co., Ltd. (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,002

(22) PCT Filed: Dec. 30, 1995

(86) PCT No.: PCT/KR95/00186

§ 371 Date: Jun. 29, 1998

§ 102(e) Date: Jun. 29, 1998

(87) PCT Pub. No.: WO97/24311

PCT Pub. Date: Jul. 10, 1997

(51) Int. Cl.[7] ................................... C07C 51/42
(52) U.S. Cl. .................. 562/486; 562/485; 562/487; 422/245.1; 422/251; 422/135
(58) Field of Search .................... 562/485, 486, 562/487; 422/245.1, 251, 135

(56) References Cited

U.S. PATENT DOCUMENTS

| Re. 36,008 | * | 12/1998 | Hindmarsh et al. | 562/414 |
|---|---|---|---|---|
| 3,584,039 | * | 6/1971 | Meyer | 562/486 |
| 3,799,976 | * | 3/1974 | Nienburg et al. | 562/487 |
| 4,467,111 | * | 8/1984 | Puskas et al. | 562/487 |
| 5,110,984 | * | 5/1992 | Janulis | 562/487 |
| 5,210,292 | | 5/1993 | Park et al. | 562/487 |

FOREIGN PATENT DOCUMENTS 2508819  2/1975 (DE).

OTHER PUBLICATIONS

Japanese Patent Unexamined Publication No. 50–104,276, dated Aug. 18, 1975.
Japanese Patent Unexamined Publication No. 61–43139, dated Mar. 1, 1986.
Japanese Patent Unexamined Publication No. 60–233033, dated Nov. 19, 1985.
Japanese Patent Unexamined Publication No. 60–216884, dated Oct. 30, 1985.
Japanese Patent Unexamined Publication No. 61–43140, dated Mar. 1, 1986.
Japanese Patent Unexamined Publication No. 60–163843, dated Aug. 26, 1985.
Japanese Patent Unexamined Publication No. 60–19784, dated Jan. 31, 1985.

\* cited by examiner

*Primary Examiner*—Gary Geist
*Assistant Examiner*—Taylor V. Oh
(74) *Attorney, Agent, or Firm*—Finnegan, Henderson, Farabow, Garrett & Dunner, L.L.P.

(57) ABSTRACT

This invention relates to a process for manufacturing terephthalic acid and more particularly, to a process for manufacturing and recovering the highly purified terephthalic acid, in accordance with the practice of this invention comprising the following procedurses: alkali weight-reduction waste water discharged from weight-reduction process in a polyester textile dyeing complex is dissolved in water, adsorbed to remove impurities, and through acid-neutralization, terephthalic acid of this invention may be obtained.

11 Claims, 1 Drawing Sheet

PROCESS FOR MANUFACTURING TEREPHTHALIC ACID

BACKGROUND OF THE INVENTION

Field of the Invention

This invention relates to a process for manufacturing terephthalic acid and more particularly, to a process for manufacturing and recovering the highly purified terephthalic acid, in accordance with the practice of this invention comprising the following procedures: alkali weight-reduction waste water discharged from weight-reduction process in a polyester textile dyeing complex is dissolved in water, adsorbed to remove impurities, and through acid-neutralization, terephthalic acid of this invention may be obtained.

"Alkali weight-reduction waste water" is a remaining reactant discharged in a weight reduction-processing stage which is designed to give the polyester textile a silky property, as well as to improve the dyeing capability by treating the polyester textile with alkali metal/earth metal hydroxide, and thereby causing a part of the textile to become depolymerization. Said alkali waste water contains a large amount of alkali metal/earth metal hydroxide, terephthalic acid alkali metal/earth metal salt and ethylene glycol. In the past, a considerable amount of alkali weight-reduction waste water, generated from the large industrial complex crowded with dyeing plants, has been discharged by a conventional waste water treatment. Besides that, the sludges neutralized with such strong acid as hydrochloric acid or sulfuric acid have been used for landfills or sea-abandonments, while the remaining reactants have been discharged by a conventional waste water treatment. Therefore, the alkali weight-reduction waste water generated from the polyester weight-reduction process has caused severe environmental problems and such treatment conventionally requires a large amount of investment for anti-pollution facilities. Recently, various methods have been proposed for the recovery of terephthalic acid from the polyester weight-reduction waste water, since said recovery may be useful not only in reusing the resources, but also in abating the enviromental problems.

The conventional processes of manufacturing and recovering terephthalic acid are as follows, using polyester weight-reduction waste water:

In Japanese Patent Unexamined Publication No. 50-104,276, terephthalic acid alkali salt was neutralized with sulfuric acid to give terephthalic acid.

In Japanese Patent Unexamined Publication No. 60-19,784, ultra-filtration was introduced to remove impurities and then, terephthalic acid was obtained through neutralization with sulfuric acid.

In Japanese Patent Unexamined Publication No. 60-163,843, alkali waste water was centrifuged and neutralized with sulfuric acid to give terephthalic acid.

In Japanese Patent Unexamined Publication No. 60-216,884, alkali waste water was passed through ion-exchange membrane to give terephthalic acid.

In Japanese Patent Unexamined Publication No. 60-233,033, alkali waste water was neutralized at 120° C. and 1.7 atm to give terephthalic acid.

In Japanese Patent Unexamined Publication No. 61-43,139, alkali waste water with low concentration was adjusted to pH 5 to 6 and pH 4 two times to deposit terephthalic acid and then, centrifuged to recover terephthalic acid.

In Japanese Patent Unexamined Publication No. 61-43,140, hydrochloric acid was added to alkali waste water until the pH of the solution became 5.4 and treated with activated charcoal. Then, the solution was again added with hydrochloric acid until the pH of the solution became 2, and terephthalic acid was obtained.

In German Patent No. 2,508,819, alkali waste water was treated with sulfuric acid at 60 to 94° C. to give terephthalic acid.

In U.S. Pat No. 5,210,292, alkali waste water was adjusted to pH 6 to 9, cooled to remove sodium sulfate and then, this material was again adjusted with sulfuric acid to pH 2 to 4 to give terephthalic acid.

These reported methods as aforementioned have also several problems as follows; a) a majority of their reactions was conducted under the severe conditions, b) excess water designed to enhance the purity of terephthalic acid, produced a considerable amount of waste water, which is economically unfeasible, c) terephthalic acid was not easily separated, through the method of modulating pH, from sodium salt generated from the neutralization reaction of alkali waste water, and d) said reported methods, which failed to illustrate some methods of removing impurities and purity-monitoring methods. Especially, these reported methods failed to remove sodium salt, by-product of acid neutralization, and it may be responsible for producing another environmental pollutants. In addition, in a process of filtering terephthalic acid as a final recovery step, the particle size of terephthalic acid should be sufficiently enlarged because small particles of terephthalic acid cause insufficient separation into solids and liquids which is responsible for reduction of recovery rate, and also make it difficult to perform the drying process.

Thus, the terephthalic acid obtained by the reported methods was not sufficient for reuse owing to reduction in recovery rate and purity and further, the purity of terephthalic acid in said reported methods was analyzed by general method instead of the method to analyze the quality of terephthalic acid. In this context, said reported methods are technically and economically unfavorable for commercialization.

BRIEF DESCRIPTION OF THE DRAWINGS

The drawing is a schematic diagram showing the process of manufacturing terephthalic acid in accordance with this invention.

SUMMARY OF THE INVENTION

Figure 1:
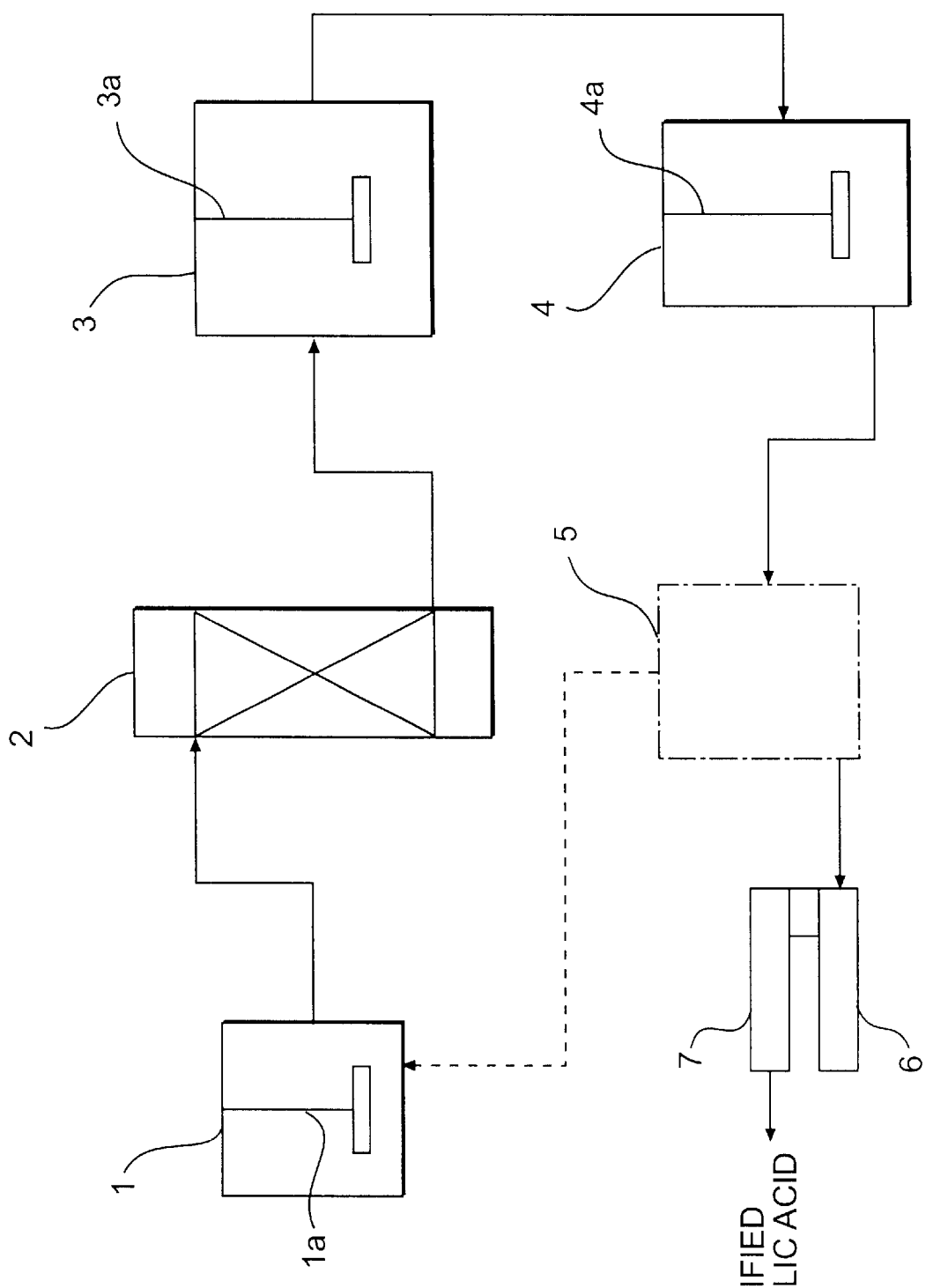

Therefore, the object of present invention is to provide a novel process for manufacturing terephthalic acid in accordance with the practice of this invention, specifically designed to obtain the following advantages: a) terephthalic acid of high purity can be obtained from alkali weight-reduction waste water, and b) sodium salt formed as a by-product in the process is separated and recovered as acid and alkali, thus reducing the production costs and abating the environmental problems.

DETAILED DESCRIPTION OF THIS INVENTION

The present invention may be described in more detail as shown below.

The present invention is characterized by a process for manufacturing terephthalic acid from alkali weight-reduction waste water comprising the following steps:

(a) a process in which an aqueous solution of alkali weight-reduction waste water dissolved in water is adsorbed;
(b) a process in which an aqueous solution is neutralized with acid to give terephthalic acid;
(c) a crystallization process to enlarge the particle of terephthalic acid;
(d) a process in which the enlarged particle of terephthalic acid is cooled under reduced pressure, filtered and dried.

The present invention also relates to several kinds of successively installed tanks for manufacturing terephthalic acid, which is characterized by the following systems: dissolving system where alkali weigh-reduction waste water is dissolved in water; centrifuge; adsorption tower; neutralization system where terephthalic acid alkali metal/earth metal salt is neutralized with acid to prepare terephthalic acid; crystallization system where the particle of terephthalic acid is enlarged; cooling system; filtering system where the enlarged particle of terephthalic acid is filtered; drying system where filtered terephthalic acid is dried.

The present invention is described in more detail as set forth hereunder.

This invention relates to a process for manufacturing and recovering terephthalic acid from a considerable amount of alkai weight-reduction waste water after the alkali weight-reduction process for polyester textile. In accordance with the practice of this invention, the highly purified terephthalic acid can be obtained in an easier manner. In addition, since the solvents and raw materials discharged in the reaction may be fed back, one can expect the reduction of production costs as well as to abate the environmental problems.

The process of manufacturing terephthalic acid according to this invention is referred in more detail to the drawings as follows:

Alkali weight-reduction waste water is charged into dissolving tank (1) together with water, then stirred by agitator (1$a$, 60 to 300 rpm) and adsorbed in adsorption tower (2) to remove the impurities.

The alkali weight-reduction waste water used in this invention refers to alkali waste material generated from the polyester textile weight-reduction process. The composition of alkali weight-reduction waste water may differ based upon the weight-reduction ratio and washing rate, or upon the type of weight-reduction process (e.g., batch operation and continuous operation). In general, alkali weight-reduction waste water (specific gravity: 1.05 to 1.35, pH: 11 to 14) discharged from the polyester textile weight-reduction process contains sodium hydroxide of 1 to 25%, disodium terephthalate of 1 to 20%, ethylene glycol, additives used in the manufacture of polyester textile, excess water and other impurities. In addition, now that the solubility of disodium terephthalate contained in alkali weight-reduction waste material to water is about 13 weight % at room temperature, it may exist in the form of slurry. Therefore, the amount of water to freely dissolve disodium terephtalate may be changed in accordance with the contents of alkali weight-reduction waste water, but about 0.5 to 2.0 times of water in weight is preferably added in proportion to alkali weight-reduction waste water. Further, in order to enhance the solubility of disodium terephthalate, the dissolving tank should be kept constant at atmospheric pressure and 25 to 80° C.

An aqueous solution containing disodium terephthalate, which is freely dissolved in dissolving tank (1), is delivered to adsorption tower (2), where some impurities (e.g., metal, metal compound, organic compound, dirt, etc.) are removed. The purity of terephthalic acid, a final product, is determined based upon the removal efficiency in adsorption tower (2).

According to this invention, activated carbon as a filling material of adsorption tower (2), which is stable in alkali solution, is selected for use and in consideration of its adsorption rate, the surface area of activated carbon per unit volume is preferably 500 to 1,500 m$^2$/g. Since the operation temperature of adsorption tower (2) is determined by that of dissolving tank (1), another heating or cooling system is unnecessary but the scope of operation pressure maintained at 0.01 to 1.0 kg/cm$^2$ is advantageous for further enhancement of adsorption rate. The residence time in adsorption tower (2) is preferably 1 to 60 mins and such residence time may be somewhat adjusted in accordance with the operation pressure. In addition, as a method of enhancing the adsorption efficiency, an aqueous solution, passed through dissolving tank (1), is prefiltered by an apparatus to separate solids and liquids, prior to delivery of adsorption tower (2). If this is the case, the efficiency of removing impurities in adsorption tower (2) may be further enhanced.

An aqueous solution of disodium terephthalate, passed through adsorption tower (2), is transferred to neutralization tank (3) for neutralization with acid. While agitating by agitator (3$a$) in neutralization tanks (3), said solution was mixed slowly with such strong acids as hydrochloric acid, sulfuric acid, nitric acid, phosphoric add. Then, disodium terephthalate is neutralized to prepare terephthalic acid and sodium salt individually. During the neutralization reaction, two equivalence points are formed; the 1st equivalence point is detected when the pH of said solution is between 9.0 and 6.0, where sodium hydroxide is neutralized with acid to prepare sodium salt, and the 2nd equivalence point is detected when the pH of said solution is between 4.0 and 2.0, where disodium terephthalate is neutralized with acid to prepare terephthalic acid. During said neutralization reaction, therefore, acid should be incessantly provided until the pH of said solution is 4.0 to 2.0.

After said neutralization reaction, the obtained sodium salt is freely soluble in water due to its larger solubility to water, while terephthalic acid in solid state is crystallized. Since the particle size of crystallized terephthalic acid is so small, terephthalic acid may not be efficiently separated by a method of separating solids and liquids (e.g., centrifugation or filtration).

Even if separated, its recovery rate is quite low and thus, the commercial application is not economically feasible. According to this invention, therefore, the slurry of terephthalic acid, so obtained from said neutralization process, is charged into crystallization tank (4) containing an agitator (4$a$) to sufficiently enlarge the particle size of terephthalic acid. One to five crystallization tanks (4) in series is/are connected and each crystallization tank (4) is operated in such a fabrication that temperature may be lowered stepwise. With said structure, the particle size may be enlarged stepwise, thus making it possible to decrease the contents of small particles. Crystallization temperature drop should be preferably 30 to 50° C. All the crystallization tanks (4) should be operatable with in the following specification: temperature in 120 to 300° C., pressure in 2 to 86 kg/cm$^2$ and agitation rate at 60 to 300 rpm. The total residence time required to completely pass through crystallization tank (4) is preferably 30 to 180 mins. In addition, since the process of terephthalic acid crystallization is conducted at high temperature and pressure, excess acid may cause corrosion of crystallization tank (4). In this connection, any acid contained in the slurry of terephthalic acid, passed through said neutralization process, should be lower than 10 weight %. Strong corrosion-resistant material should be selected such as stainless steel type 316 or titanium for crystallization tank.

The sufficiently enlarged terephthalic acid in said crystallization tank (4) is charged into the next cooling tank (5) and cooled at reaction pressure of 0.1 to 1.0 kg/cm² and temperature of 60 to 90 ° C. under reduced pressure. Hence, the evaporated water is condensed and fed back to dissolving tank (1).

The slurry of cooled terephthalic acid is delivered to filter (6) to separate solids and liquids. The operation temperature of filter (6) depends on the slurry temperature of terephthalic acid and the temperature is preferably maintained at 60 to 80° C. The pressure is preferably 0.1 to 0.8 kg/cm².

Based upon said method of separating solids and liquids, terephthalic acid is separated as wet cake, and sodium salt is separated in liquid state together with water. The filtered terephthalic acid is washed with water and in consideration of washing efficiency, 0.5 to 1.2 times of water to terephthalic acid (30 to 80° C.) in proportion to terephthalic acid is preferably used.

The filtered terephthalic acid is charged into dryer (7) and dried at pressure of 0.5 to 1.0 kg/cm² and temperature of 100 to 150° C. for 10 to 120 mins, to give terephthalic acid, a final product of this invention.

As described in the above, this invention is intended to provide a process for reusing the feed-back reacting raw materials including solvents discharged from each manufacturing step, thus making it possible to reduce product costs and also to abate environmental problems caused by waste scrap materials. Further, terephthalic acid, so separated and recovered from said manufacturing process, may be obtained with a high yield of 98% or better.

This invention is explained in more detail by the following examples, but the claims are not limited to these examples.

EXAMPLE 1

100 g of alkali weight-reduction waste water (pH: 11.4), collected from polyester textile process to reduce 11.0% in a continuous operation, was charged into dissolving tank (1), added with 50 g of water and stirred by agitator (1a, 60 rpm) at atmospheric pressure and room temperature for 15 mins.

An aqueous solution of disodium terephthalate, passed through dissolving tank (1), was transferred to adsorption tower (2) and adsorbed at pressure of 1 kg/cm² and temperature of 25° C. for 60 mins. The adsorption tower (2) was filled with activated charcoal of surface area of 500 m²/g.

An aqueous solution of disodium terephthalate, passed through adsorption tower (2), was transferred to neutralization tank (3). Then, the solution was stirred by agitator (3a) in neutralization tank and added slowly with hydrochloric acid and incessantly until the pH of reaction solution was 4.0. As a result of monitoring by SEM the particle of terephthalic acid formed from said neutralization process, its particle size (5 to 15 μm) was very small.

Said neutralization solution was charged into crystallization tank (4) to enlarge the particle size of terephthalic acid. The crystallization tank is of stainless steel type 316 and has the following reaction requirements: temperature in 150° C., pressure in 5 kg/cm² and agitation rate at 60 rpm. (4a) The residence time was 30 mins.

The sufficiently enlarged slurry of terephthalic acid in said crystallization tank (4) was charged into the next cooling tank (5) and cooled under reduced pressure, at pressure of 0.1 kg/cm² and temperature of 60° C. Hence, the evaporated methanol and water were condensed and fed back to dissolving tank (1). The slurry of cooled terephthalic add was delivered to filter (6) to individually separate solids and liquids, at pressure of 0.8 kg/cm² and temperature of 60° C. Then, terephthalic acid in wet cake was recovered. The filtered terephthalic acid was charged into dryer (7) and dried at reaction pressure of 0.5 kg/cm² and temperature of 120° C. for 60 mins to give 2.05 g of terephthalic acid.

EXAMPLE 2

In accordance with the same process as did in said EXAMPLE 1, terephthalic acid was manufactured and recovered but 97% sulfuric acid in neutralization tank (3) was constantly added until the pH of reaction solution became 2.0.

EXAMPLE 3

100 g of alkali weight-reduction waste water (pH: 13.3), collected from polyester textile process to reduce 20% in a batch operation and precipitated with disodium terephthalate, was charged into dissolving tank (1), added with 200 g of water and stirred by agitator (1a, 60 rpm) at atmospheric pressure and 80° C. for 10 mins.

An aqueous solution of disodium terephthalate, passed through dissolving tank (1), were transferred to adsorption tower (2) and adsorbed at pressure of 0.1 kg/cm² and 80° C. for 60 mins. The adsorption tower (2) was filled with activated charcoal of surface area of surface area of 1,500 m²/g.

An aqueous solution of disodium terephthalate, passed through adsorption tower (2), was transferred to neutralization tank (3). Then, the solution was stirred by agitator (3a) in neutralization tank and added slowly with sulfuric acid and incessantly until the pH of reaction solution was 2.0. As a result of monitoring by SEM the particle of terephthalic acid formed from said neutralization process, its particle size (10 to 15 μm) was very small.

In this connection, said neutralization solution was charged into crystallization tank (4) to enlarge the particle of terephthalic acid. The crystallization tank (4) is of stainless steel type 316 or titanium which was connected with five crystallization tanks in series and each of crystallization tank has the following reaction requirements: pressure in 2 to 86 kg/cm² and agitation rate at 150 to 300 rpm. In addition, the temperature of the first crystallization tank was determined at 300° C. in such a fabrication that the temperature of said crystallization tank was lowered to 30 to 50° C. and the total residence time, passed through the whole crystallization tank (4), was 180 mins.

The sufficiently enlarged slurry of terephthalic acid in said crystallization tank (4) was charged into the next cooling tank (5) and cooled under reduced pressure, at pressure of 1.0 kg/cm² and temperature of 90° C. Hence, the evaporated water were condensed and fed back to dissolving tank (1). The slurry of cooled terephthalic acid was delivered to filter (6) to individually separate solids and liquids, at pressure of 0.1 kg/cm² and temperature of 80° C. Then, terephthalic acid in wet cake was recovered. The filtered terephthalic acid was charged into dryer (7) and dried at pressure of 1.0 kg/cm² and temperature of 150° C. for 120 mins to give 35.2 g of terephthalic acid.

EXPERIMENT

Each of terephthalic acid, so obtained from said EXAMPLE 1 to 3, was analyzed by the following methods:

(1) Recovery rate (%) =

$$\frac{\text{recovered amount of terephthalic acid}}{\text{amount of alkai weight-reduction waste waste water} \times \text{conc. of disodiumterephthalate} \times 0.791} \times 100$$

(2) Purity: As for terephthalic acid, so obtained from PET, μ-bondapak C18 column was introduced to monitor the concentration of its impurities on high pressure liquid chromatography (HPLC).
(3) Average particle size: Sieve analysis method and SEM were introduced to monitor average particle size.
(4) Transmittance: With a solution prepared by dissolving terephthalic acid in an aqueous solution of potassium hydroxide, spectrometer SPECTRONIC 601(MILTON ROY) was introduced to monitor its transmittance at 340 nm.
(5) Color value: DIANO Match Scan II Colorimeter was introduced to monior the values of color L, a and b.
(6) Metal content: XRF (X-ray refractive fluorescence) was introduced to monitor the metal content of Co, Mn and Fe.

TABLE

|  | EXAMPLE | | |
| --- | --- | --- | --- |
|  | 1 | 2 | 3 |
| Recovery rate (%) | 98.3 | 98.7 | 99.6 |
| Purity (%) | 99.7 | 99.8 | 98.4 |
| Average particle size (μm) | 38 | 42 | 97 |
| Transmittance (%) | 72 | 71 | 59 |
| Color value | | | |
| L | 97.01 | 97.39 | 95.87 |
| a | −00.5 | 0.06 | 0.15 |
| b | 1.64 | 1.58 | 2.62 |
| Metal content (ppm) | | | |
| Co | 0.2 | 0.2 | 0.3 |
| Mn | 0 | 0 | 0.1 |
| Fe | 3.5 | 2.6 | 11.4 |

Therefore, now that terephthalic acid recovered by the methods of this invention does not contain any metals and also maintain a high purity, it is very useful in preparing polyester resin.

What is claimed is:

1. A process for manufacturing terephthalic acid from alkali weight reduction waste water, comprising:
    separating dialkali terephthalic acid from impurities to produce a separated aqueous solution comprising dialkali terephthalic acid, said separating comprising adsorbing said alkali weight reduction waste water onto a filling material, wherein said alkali weight reduction water has a pH above the first equivalence point of terephthalic acid and comprises dialkali terephthalic acid; and thereafter:
    neutralizing said separated aqueous solution which comprises dialkali terephthalic acid with acid to produce terephthalic acid;
    crystallizing said terephthalic acid to enlarge the particle size of the crystals of terephthalic acid;
    cooling said enlarged crystals of terephthalic acid;
    filtering said enlarged crystals of terephthalic acid; and
    drying said enlarged crystals of terephthalic acid.

2. The process according to claim 1, wherein said filling material is activated carbon.

3. The process according to claim 1, wherein said alkali weight reduction waste water has an origin chosen from waste waters discharged from polyester textile processes.

4. The process according to claim 1, wherein said crystallizing occurs in at least one crystallization tank.

5. The process according to claim 4, wherein said at least one crystallization tank is maintained at a pressure ranging from 2 to 86 kg/cm² and at a temperature ranging from 120 to 300° C.

6. The process according to claim 1, wherein said crystallizing occurs in at least one crystallization tank which is maintained at a pressure ranging from 2 to 86 kg/cm² and a temperature ranging from 120 to 300° C.

7. The process according to claim 1, wherein said crystallizing occurs in from 2 to 5 crystallization tanks connected in series.

8. The process according to claim 7, wherein the temperature of each of said 2 to 5 crystallization tanks is 30 to 50° C. lower in temperature than of each previous crystallization tank.

9. The process according to claim 1, wherein said cooling occurs at a pressure ranging from 0.1 to 1.0 kg/cm² and at a temperature ranging from 60 to 90° C.

10. The process according to claim 1, further comprising:
    filtering said alkali weight reduction waste water before adsorbing said alkali weight reduction waste water onto a filling material.

11. An apparatus for manufacturing terephthalic acid from alkali weight reduction waste water, comprising:
    a dissolving tank for containing said alkali weight reduction waste water;
    a centrifuge in communication with said dissolving tank;
    an absorption tower in communication with said centrifuge;
    a neutralization tank which is in communication with said adsorption tower and wherein said alkali weight reduction waste water is neutralized to produce terephthalic acid;
    a crystallization tank which is in communication with said neutralization tank and wherein enlarging the particle size of the crystals of terephthalic acid may occur;
    a cooling system which is in communication with said dissolving tank and said crystallization tank;
    a filtering system which is in communication with said cooling system and wherein the enlarged crystals of terephthalic acid are filtered; and
    a drying system which is in communication with said filtering system.

* * * * *